United States Patent [19]
Tanaka et al.

[11] Patent Number: 6,051,606
[45] Date of Patent: Apr. 18, 2000

[54] PESTICIDAL COMPOSITION

[75] Inventors: Yasuyori Tanaka; Takao Ishiwatari, both of Toyonaka, Japan

[73] Assignee: Sumitomo Chemical Company, Limited, Osaka, Japan

[21] Appl. No.: 09/368,182

[22] Filed: Aug. 4, 1999

[30] Foreign Application Priority Data

Aug. 10, 1998 [JP] Japan ................... 10-225763

[51] Int. Cl.⁷ .................... A01N 53/00; A01N 31/02; A01N 53/02
[52] U.S. Cl. ................ 514/531; 514/531; 424/405
[58] Field of Search ............... 514/531; 424/405

[56] References Cited

PUBLICATIONS

Tanaka Y. et al. (CA 127:105644, abstract of JP 09177915), 1997.
Arthur and E. Rose (The condensed Medical Dictionary, Sixth Edition, p. 409, Reinold Publishing Corporation, New York), 1963.

*Primary Examiner*—Jose G. Dees
*Assistant Examiner*—Sabiha N. Qazi
*Attorney, Agent, or Firm*—Sughrue, Mion, Zinn, Macpeak & Seas, PLLC

[57] ABSTRACT

Provided are pesticidal compositions comprising (i) 2-methyl-4-oxo-3-(2-propynyl)cyclopent-2-enyl 3-(2,2-dichlorovinyl)-2,2-dimethylcyclopropanecarboxylate, and (ii) propylene glycol monoalkyl ether or dipropylene glycol monoalkyl ether. In addition, methods of controlling pests which comprise utilizing said composition are provided.

10 Claims, No Drawings

PESTICIDAL COMPOSITION

BACKGROUND OF THE INVENTION

1. Field of the Invention

The instant invention relates to pesticidal compositions, and methods of controlling pests.

2. Description of Related Art

South African patent 80-4391 discloses 2-methyl-4-oxo-3-(2-propynyl) cyclopent-2-enyl 3-(2,2-dichlorovinyl)-2,2-dimethylcyclopropanecarboxylate as an active ingredient of a pesticide, but 2-methyl-4-oxo-3-(2-propynyl) cyclopent-2-enyl 3-(2,2-dichlorovinyl)-2,2-dimethylcyclopropanecarboxylate does not always provide sufficient rapid activity when provided in pesticidal compositions, and more particularly, pesticidal aerosol compositions. The rapid activity which is desirous for such compositions should allow a pesticidal composition to control a pest quickly after said pesticidal composition is utilized on said pest.

Japanese unexamined patent publication No. Hei 2-304004-A discloses propylene glycol monoalkyl ethers and dipropylene glycol dialkyl ethers as active ingredients of a termite-controlling agent. However, in order to control pests, the efficacy of the propylene glycol monoalkyl ethers and dipropylene glycol dialkyl ethers in the termite-controlling agent is not satisfactory.

SUMMARY OF THE INVENTION

The instant invention provides a pesticidal composition possessing excellent pesticidal activity and a method of controlling pests. In this regard, the pesticidal compositions of the instant invention possess an unexpectedly superior pesticidal activity when compared with a composition comprising 2-methyl-4-oxo-3-(2-propynyl)cyclopent-2-enyl 3-(2,2-dichlorovinyl)-2,2-dimethylcyclopropanecarboxylate as an active ingredient, without the below glycol derivatives. For example, the pesticidal activity in the inventive pesticidal compositions provides a rapid activity, such that the provided pesticidal composition can quickly control a pest after said pest has been exposed to said pesticidal composition.

Particularly, the instant invention provides novel pesticidal compositions comprising 2-methyl-4-oxo-3-(2-propynyl)cyclopent-2-enyl 3-(2,2-dichlorovinyl)-2,2-dimethylcyclopropanecarboxylate and a specified glycol derivative, as well as a method of controlling pests which comprises utilizing the inventive pesticidal compositions, wherein the glycol derivative in the pesticidal compositions of the instant invention is a propylene glycol monoalkyl ether, dipropylene glycol monoalkyl ether, or the like.

DETAILED DESCRIPTION OF THE INVENTION

A pesticidal composition of the instant invention typically comprises (i) 2-methyl-4-oxo-3-(2-propynyl)cyclopent-2-enyl 3-(2,2-dichlorovinyl)-2,2-dimethylcyclopropanecarboxylate and (ii) a specified glycol derivative, wherein a weight to weight ratio of 2-methyl-4-oxo-3-(2-propynyl)cyclopent-2-enyl 3-(2,2-dichlorovinyl)-2,2-dimethylcyclopropanecarboxylate to the glycol derivative in the pesticidal compositions of the instant invention is preferably about 1:3 to 1:100.

Suitable glycol derivatives which can be utilized in the pesticidal compositions typically include propylene glycol monoalkyl ethers or dipropylene glycol monoalkyl ethers, and the like. In such cases, the propylene glycol monoalkyl ethers which are utilized in the pesticidal compositions of the instant invention are preferably encompassed by the following formula (I):

$$R^1OC_3H_6OH \quad \quad (I)$$

wherein, $R^1$ represents an alkyl group. Further, in formula (I), $R^1$ preferably represents a $C_{1-4}$ lower alkyl group such as methyl, ethyl, n-propyl, isopropyl, n-butyl, isobutyl, sec-butyl, tert-butyl group, or the like, and more preferably an ethyl group or methyl group, and most preferably a methyl group. Said propylene glycol monoalkyl ether is most preferably a 1-alkoxy-2-propanol compound, such as 1-methoxy-2-propanol.

In the event that the inventive pesticidal compositions comprise a dipropylene glycol monoalkyl ether therein as said glycol derivative, said dipropylene glycol monoalkyl ether is preferably encompassed by the following formula (II):

$$R^2OC_3H_6OC_3H_6OH \quad \quad (II)$$

wherein, $R^2$ represents an alkyl group. Further, in formula (II), $R^2$ preferably represents a $C_{1-4}$ lower alkyl group such as methyl, ethyl, n-propyl, isopropyl, n-butyl, isobutyl, sec-butyl, tert-butyl group, or the like, and more preferably an ethyl group, methyl group or the like, and most preferably a methyl group. Said dipropylene glycol monoalkyl ethers is most preferably a compound encompassed by the following formula (III) or (IV):

$$R^2OCHCH_2OCHCH_2OH \quad \quad (III)$$
$$\phantom{R^2O}\overset{|}{CH_3}\phantom{CH_2O}\overset{|}{CH_3}$$

$$R^2OCHCH_2OCH_2CHOH \quad \quad (IV)$$
$$\phantom{R^2O}\overset{|}{CH_3}\phantom{CH_2OCH_2}\overset{|}{CH_3}$$

wherein $R^2$ is the same as defined above.

2-methyl-4-oxo-3-(2-propynyl)cyclopent-2-enyl 3-(2,2-dichlorovinyl)-2,2-dimethylcyclopropanecarboxylate is generally present in the pesticidal compositions of the instant invention at an amount of from about 0.001 to 30% by weight, based on the total weight of the provided composition. Various optical or geometrical isomers thereof may be present in the pesticidal compositions of the instant invention as 2-methyl-4-oxo-3-(2-propynyl)cyclopent-2-enyl 3-(2,2-dichlorovinyl)-2,2-dimethylcyclopropanecarboxylate, provided that said optical or geometrical isomers in the pesticidal compositions of the instant invention are pesticidally active.

The pesticidal compositions of the instant invention typically comprise the glycol derivative in an amount of from about 0.003 to 99% by weight, and preferably about 0.003 to 91% by weight, based on the total weight of the provided composition.

The pesticidal compositions of the instant invention are typically produced or formulated by forming a mixture of 2-methyl-4-oxo-3-(2-propynyl)cyclopent-2-enyl 3-(2,2-dichlorovinyl)-2,2-dimethylcyclopropanecarboxylate and a suitable glycol derivative at room temperature or under heated conditions. Further, the pesticidal compositions of the instant invention may be produced by additionally dissolving or adding a synergist, fragrance, solvent, solid carrier, other pesticidal compound or the like, into the mixture of 2-methyl-4-oxo-3-(2-propynyl)cyclopent-2-enyl 3-(2,2-dichlorovinyl)-2,2-dimethylcyclopropanecarboxylate and the glycol derivative, if so desired. In the event that the inventive pesticidal composition are formulated as an aerosol composition, said aerosol composition should typically further comprise a propellant.

The propellants which are utilized in the aerosol formulations of the inventive pesticidal compositions are typically contained therein at an amount of from about 20 to 90% by weight, based on the total weight of the provided composition. Examples of propellants which may be in the aerosol formulations of the instant invention include propane/butane, dimethyl ether, and the like, or combinations thereof.

Examples of the synergists which may be utilized in the pesticidal compositions of the instant invention, if so desired, include PBO, MGK 264, S421, and the like.

Examples of the solvents which may be utilized in the pesticidal compositions of the instant invention, if so desired, include kerosene; alkylbenzene such as xylene, trimethyl benzene and dodecylbenzene; diphenyl methanes such as phenylxylylethane; alcohols such as isopropanol; and the like.

Examples of solid carriers which may be utilized in the aerosol formulations of the instant invention, if so desired, include talc, clay, diatomaceous earth, pearlite, gypsum, silica and the like.

Examples of the other pesticidal compounds which may be utilized in the pesticidal compositions of the instant invention, if so desired, include allethrin, tetramethrin, prallethrin, phenothrin, resmethrin, cyphenothrin, permethrin, cypermethrin, deltamethrin, cyfluthrin, d-furamethrin, imiprothrin, etofenprox, dichlorvos, fenitrothion, propoxur, pyriproxyfen, methoprene, hydroprene, diflubenzuron, cyromazine, and the like.

The inventive methods of controlling pests generally comprise utilizing a pesticidal composition of the instant invention. Such methods of the instant invention may utilize an effective amount of the inventive pesticidal compositions for household purposes such as for controlling indoor flies, mosquitoes, cockroaches, ants or the like. In cases in which the pesticidal compositions are utilized to control flying insects such as flies, mosquitoes or the like, the methods of the instant invention should typically comprise applying an inventive pesticidal composition to a pest or a locus that the pest inhabits, so that the 2-methyl-4-oxo-3-(2-propynyl) cyclopent-2-enyl 3-(2,2-dichlorovinyl)-2,2-dimethylcyclopropanecarboxylic and the glycol derivative in the composition are applied at a combined amount of from about 0.001 to 10 mg per 1 $m^3$ of a locus that is being treated therewith. In cases in which the inventive compositions are utilized to control crawling insects such as cockroaches, ants or the like, the methods of the instant invention should typically comprise applying an inventive pesticidal composition to a pest or a locus that the pest inhabits, so that 2-methyl-4-oxo-3-(2-propynyl)cyclopent-2-enyl 3-(2,2-dichlorovinyl)-2,2-dimethylcyclopropanecarboxylate and the glycol derivative in the composition are applied at a combined amount of from about 0.01 to 100 mg per 1 $m^2$ of a locus that is being treated therewith.

For example, in the event of controlling pests of wood materials such as *Reticulitermes speratus*, Formosan subterranean termite or the like, the inventive pesticidal compositions can be directly utilized on said pests, or utilized on wood materials or soil which said pests may come in contact therewith.

The methods of the instant invention may also utilize the inventive pesticidal compositions by diluting said composition, if so desired. Typically, when an inventive pesticidal liquid formulation is utilized in the methods of the instant invention, said liquid formulation is diluted so that 2-methyl-4-oxo-3-(2-propynyl)cyclopent-2-enyl 3-(2,2-dichlorovinyl)-2,2-dimethylcyclopropanecarboxylate therein is diluted to a concentration of from about 0.001 to 5% by weight, based on the total weight of the diluted composition.

Examples of pests which are controlled by utilizing the pesticidal compositions of the instant invention include Arthropoda (insects, acarina, and the like) such as Lepidoptera, Diptera, cockroaches (Dictyoptera), Hymenoptera, Siphonaptera, lice (Anoplura), termites (Isoptera), Hemiptera, Coleoptera, thrips (Thysanoptera), Orthoptera, mites or ticks (Acarina), other well known noxious pests or the like. More specific examples of the Lepidoptera which are controlled with the methods of the instant invention include Pyralidae such as rice stem borer (*Chilo suppressalis*), rice leaf roller (*Cnaphalocrocis medinalis*) and Indian meal moth (*Plodia interpunctella*), Noctuidae such as tobacco cutworm (*Spodoptera litura*), rice armyworm (*Pseudaletia separata*) and cabbage armyworm (*Mamestra brassicae*), Pieridae such as common cabbageworm (*Pieris rape crucivora*), Tortricidae such as Adoxophyes spp., Carposinidae, Lyonetiidae, Lymantriidae, agrotis (Agrotis spp.) such as turnip cut worm (*Agrothis segetum*) and black cutworm (*Agrothis ipsilon*), Helicovera (Helicovera spp.), heliothis (Heliothis spp.), diamondback moth (*Plutella xylostella*), rice skipper (*Parnara guttata*), casemaking clothes moth (*Tinea pellinella*), webbing clothes moth (*Tineola bisselliella*), Indian meal moth (*Plodia interpunctella*), oriental moth (*Monema flavescens*), oriental tussock moth (*Euproctis subflava*), and the like. More specific examples of the Diptera which are controlled with the methods of the instant invention include mosquitoes such as common mosquito (*Culex pipens pallens*) and *Culex tritaeniorhynchus*, Aedes spp. such as yellow fever mosquito (*Aedes aegypti*) and *Aedes alpopictus*, Anopheles spp. such as *Anopheles sinensis* and *Anopheles stephensi*, midges (Chironomidae), Muscidae such as housefly (*Musca domestica*), false housefly (*Muscina stabulans*) and little housefly (*Fannia canicularis*), Calliphoridae, Sarcophagidae, Anthomyiidae such as seedcom maggot (*Delia platura*) and onion maggot (*Delia antiqua*), fruit flies (Tephritidae), vinegar flies (Drosophilidae), moth flies (Psychodidae), Phoridae, breeze flies (Tabanidae), black flies (Simuliidae), stable flies (Stomoxyidae), biting midges (Ceratopogonidae), and the like. More specific examples of the cockroaches which are controlled with the methods of the instant invention include German cockroach (*Blattella germanica*), smoky brown cockroach (*Periplaneta fuliginosa*), American cockroach (*Periplaneta americana*), brown cockroach (*Periplaneta brunnea*), Oriental cockroach (*Blatta orientalis*), and the like. More specific examples of the Hymenoptera which are controlled with the methods of the instant invention include ants (Formicidae), hornets/wasps (Vespidae), Bethylidae, sawflies (Tenthredinidae) such as cabbage sawflies (*Athalia rosae ruficornis*), and the like. More specific examples of the Siphonaptura which are controlled with the methods of the instant invention include dog fleas (*Ctenocephalides canis*), cat fleas (*Ctenocephalides felis*), human fleas (*Pulex irritans*), and the like. More specific examples of the lice (Anoplura) which are controlled with the methods of the instant invention include *Pediculus humanus humanus*, crab louse (*Pthirus pubis*), and the like. More specific examples of the termites (Isoptera) which are controlled with the methods of the instant invention include *Reticulitermes speratus*, Formosan subterranean termite (*Coptotermes sormosanus*), and the like. More specific examples of the Hemiptera which are controlled with the methods of the instant invention include planthoppers (Delphacidae) such as small brown plant hopper (*Laodelphax striatellus*), brown planthopper (*Nilaparvata lugens*) and white-backed rice planthopper (*Sogatella furcifera*), leafhoppers (Deltocephalidae) such as green rice leafhopper (*Nephotettix cincticeps*) and green rice leafhopper (*Nephotettix virescens*), aphids (Aphididae), plant bugs (Heteroptera), whiteflies (Aleyrodidae), scales, lace bugs (Tingidae), jumping plantlice (Psyllidae), Cimicidae, and the like. More specific examples of the Coleoptera which are controlled with the methods of the instant invention include corn rootworms such as black carpet beetle (*Attagenus unicolor japonicus*), varied carpet beetle (*Authrenus verbasci*), western corn rootworm (*Diabrotica virgifera*) and southern corn rootworm (*Diabrotica undecimpunctata howardi*), scarabs (Scarabaeidae) such as cupreous chafer (*Anomala cuprea*) and soybean beetle (*Anomala rufocuprea*), weevils (Curculionidae) such as maize weevil (*Sitophilus zeamais*), rice water weevil (*Lissorhoptrus oryzophilus*), ball weevil and adzuki bean weevil (*Callosobruchus chinensis*), darkling beetles (Tenebrionidae) such as yellow mealworm (*Tenebrio molitor*) and red flour beetle (*Tribolium castaneum*), leaf beetles (Chrysomelidae) such as rice leaf beetle (*Oulema oryzae*), striped flea beetle (*Phyllotreta striolata*) and cucurbit leaf beetle (*Aulacophora femoralis*), deathwatch beetles (Anobiidae), Epilachna (Epilachna spp.) such as twenty-eight-spotted ladybird (*Epilachna Vigintioctopunctata*), powderpost beetles (Lyctidae), lesser grain borers (*Rhizopertha dominica*), beet tortoise beetles (*Cassida nebulosa*), robe beetles (*Paederus fuscipes*), and the like. More specific examples of the thrips (Thysanoptera) which are controlled with the methods of the instant invention include *Thrips palmi*, western flower thrips, flower thrips (*Thrips hawaiiensis*), and the like. More specific examples of the Orthoptera which are controlled with the methods of the instant invention include mole cricket (Gryllotalpa sp.), grasshoppers (Acrididae), and the like. More specific examples of the mites or ticks which are controlled with the methods of the instant invention include Dermanyssidae such as American house dust mite, *Dermatophagoides frarinae* and *Dermatophagoides pteronyssinus*, Acaridae such as mold mite (*Tyrophagus putrescentiae*) and brown legged grain mite (*Aleuroplyphus ovatus*), Glycyphagidae such as *Glycyphagus privatus, Glycyphagus domesticus* and *Glycyphagus destructor*, Cheyletidae such as *Chelacaropsis malaccensis, Cheyletus fortis* and *Chelacaropsis moorei*, Tarsonemidae, chortoglyphus spp., *Halplochthonis simplex*, spider mites (Tetranychidae) such as two-spotted spider mite (*Tetranychus urticae*), Kanzawa spider mite (*Tetranychus kanzawai*), citrus red mite (*Panonychus citri*) and European red mite (*Panochychus ulmi*), Ixodidae such as *Haemaphxalis longicornis*, and the like. More specific examples of the other pests which are controlled with the methods of the instant invention include spiders (Araneida) such as black widow (Lactrodectus) and *Chiracanthium japonicum*, millepedes (millipeda), centipedes (centipeda), sow bugs, pill bugs (Armadillida), and the like.

EXAMPLES

Hereinafter, the instant invention is explained in further detail through the examples, but the instant invention is not limited to the examples.

Formulation Example 1

One (1) part by weight of (S)-2-methyl-4-oxo-3-(2-propynyl) cyclopent-2-enyl (1R)-trans-3-(2,2-dichlorovinyl)-2,2-dimethylcyclopropanecarboxylate (hereinafter referred to as Compound A) and 10 parts by weight of propylene glycol monomethyl ether (ARCO Chemical Company, product name: Arcosolv PM) are mixed together at room temperature, to achieve a pesticidal composition of the instant invention.

Formulation Example 2

One (1) part by weight of Compound A and 100 parts by weight of propylene glycol monomethyl ether (ARCO Chemical Company, product name: Arcosolv PM) are mixed together at room temperature, to achieve a pesticidal composition of the instant invention.

Formulation Example 3

One (1) part by weight of Compound A and 10 parts by weight of dipropylene glycol monomethyl ether (ARCO Chemical Company, product name: Arcosolv DPM) are mixed together at room temperature, to achieve a pesticidal composition of the instant invention.

Formulation Example 4

One (1) part by weight of Compound A and 100 parts by weight of dipropylene glycol monomethyl ether (ARCO Chemical Company, product name: Arcosolv DPM) are mixed together at room temperature, to achieve a pesticidal composition of the instant invention.

Formulation Example 5

One (1) part by weight of Compound A and 10 parts by weight of propylene glycol monoethyl ether (ARCO Chemical Company, product name: Arcosolv PE) are mixed together at room temperature, to achieve a pesticidal composition of the instant invention.

Formulation Example 6

One (1) part by weight of Compound A, 10 parts by weight of 1-methoxy-2-propanol and 89 parts by weight of kerosene are mixed together at room temperature, to achieve a pesticidal composition of the instant invention.

Formulation Example 7

Five (5) parts by weight of Compound A, 15 parts by weight of 1-ethoxy-2-propanol and 80 parts by weight of kerosene are mixed together at room temperature, to achieve a pesticidal composition of the instant invention.

Formulation Example 8

Fifty (50) parts by weight of the pesticidal composition obtained in Formulation Example 6 are packed into an aerosol container. After attaching a valve to the aerosol container, 50 parts by weight of dimethyl ether are charged into the aerosol container through the valve, to achieve a pesticidal composition of the instant invention.

Formulation Example 9

Two (2) parts by weight of 1-ethoxy-2-propanol and 0.10 parts by weight of Compound A, 9.9 parts by weight of an anhydrous silica, and 2 parts by weight of isopropyl myristate are packed into an aerosol container. After attaching a valve to the aerosol container, 86 parts by weight of dimethyl ether are charged into the aerosol container through the valve, to achieve an aerosol formulation of the instant invention.

Comparative Formulation Example 1

One (1) part by weight of Compound A and 10 parts by weight of 3-methoxy-3-methyl-1-butanol are mixed together at room temperature, to achieve a pesticidal composition.

Comparative Formulation Example 2

One (1) part by weight of Compound A and 100 parts by weight of 3-methoxy-3-methyl-1-butanol are mixed together at room temperature, to achieve a pesticidal composition.

Comparative Formulation Example 3

One (1) part by weight of Compound A and 10 parts by weight of isopropanol are mixed together at room temperature, to achieve a pesticidal composition.

Comparative Formulation Example 4

One (1) part by weight of Compound A and 100 parts by weight of isopropanol are mixed together at room temperature, to achieve a pesticidal composition.

Comparative Formulation Example 5

One (1) part by weight of Compound A and 10 parts by weight of tripropylene glycol monomethyl ether (ARCO Chemical Company, product name: Arcosolv TPM) are mixed together at room temperature, to achieve a pesticidal composition.

Comparative Formulation Example 6

One (1) part by weight of Compound A and 10 parts by weight of dibutyl phthalate are mixed together at room temperature, to achieve a pesticidal composition.

Comparative Formulation Example 7

One part by weight of Compound A and 100 parts by weight of dibutyl phthalate are mixed together at room temperature, to achieve a pesticidal composition.

Test Examples 1 to 5 and Comparative Test Examples 1 to 7

Each of the pesticidal compositions of Formulation Examples 1 to 5 and Comparative Formulation Examples 1 to 7 were diluted with deodorized kerosene so that the concentration of Compound A therein was 0.1% weight/volume.

A 20 cm×20 cm piece of paper was laid over each metal mesh which was set on the bottom area of a 46 cm×46 cm×70 cm metallic chamber, respectively. A container wherein said container had a diameter of 8.75 cm, a height of 7.5 cm, 5 male and 5 female German cockroaches present therein, a 16 mesh metal mesh overlaid on the bottom area thereof, as well as butter spread on the wall surfaces thereof, was deposited onto each of said 20 cm×20 cm piece of papers.

Three-quarters milliliters (0.75 mL) of the diluted pesticidal compositions were then sprayed from above said chambers, respectively, in the direction of the cockroaches, at a pressure of 0.42 kg/cm$^2$, and by use of a spray gun. Each of the containers was removed from the chambers 30 seconds thereafter, and the German cockroaches were transferred into plastic cups. The time needed to knock down the German cockroaches in each of the plastic cups was examined. The tests were performed at least 2 times. The averages of the results are shown in Table 1.

TABLE 1

| Test Example # | The Pesticidal Oily Composition | The Time needed to knockdown all the insects (minutes) |
| --- | --- | --- |
| 1 | Formulation Example 1 | 3 |
| 2 | Formulation Example 2 | 3 |
| 3 | Formulation Example 3 | 5 |
| 4 | Formulation Example 4 | 5 |
| 5 | Formulation Example 5 | 1.5 |
| Comparative 1 | Comparative Formulation Example 1 | more than 10 |
| Comparative 2 | Comparative Formulation Example 2 | more than 10 |
| Comparative 3 | Comparative Formulation Example 3 | more than 10 |
| Comparative 4 | Comparative Formulation Example 4 | more than 10 |
| Comparative 5 | Comparative Formulation Example 5 | more than 10 |
| Comparative 6 | Comparative Formulation Example 6 | more than 10 |
| Comparative 7 | Comparative Formulation Example 7 | more than 10 |

The results of the above test and comparative examples evidence that the pesticidal compositions of the instant invention provide an excellent pesticidal activity and that the removal of the glycol derivative therefrom or the use of another solvent does not result in such surprisingly advantageous results.

Each of the patent documents and publications that are mentioned in the instant specification are incorporated herein by reference in their entirety.

What is claimed is:

1. A pesticidal composition comprising:

(i) 2-methyl-4-oxo-3-(2-propynyl)cyclopent-2-enyl 3-(2,2-dichlorovinyl)-2,2-dimethylcyclopropanecarboxylate, and (ii) a propylene glycol monoalkyl ether or a dipropylene glycol monoalkyl ether.

2. The pesticidal composition according to claim 1, wherein a weight to weight ratio of (i) 2-methyl-4-oxo-3-(2-propynyl)cyclopent-2-enyl 3-(2,2-dichlorovinyl)-2,2-dimethylcyclopropanecarboxylate to (ii) the propylene glycol monoalkyl ether or the dipropylene glycol monoalkyl ether in said pesticidal composition is from 1:3 to 1:100.

3. The pesticidal composition according to claim 1, wherein the composition comprises:

(i) 2-methyl-4-oxo-3-(2-propynyl)cyclopent-2-enyl 3-(2,2-dichlorovinyl)-2,2-dimethylcyclopropanecarboxylate, and (ii) the propylene glycol monoalkyl ether.

4. The pesticidal composition according to claim 1, wherein the composition comprises:

(i) 2-methyl-4-oxo-3-(2-propynyl)cyclopent-2-enyl 3-(2,2-dichlorovinyl)-2,2-dimethylcyclopropanecarboxylate, and (ii) the dipropylene glycol monoalkyl ether.

5. The pesticidal composition according to claim 3, wherein the propylene glycol monoalkyl ether is a propylene glycol monomethyl ether or propylene glycol monoethyl ether.

6. The pesticidal composition according to claim 4, wherein the dipropylene glycol monoalkyl ether is a dipropylene glycol monomethyl ether.

7. The pesticidal composition according to claim 1, wherein the composition further comprises a propellant.

8. The pesticidal composition according to claim 1, wherein the composition further comprises a propellant and a solid carrier.

9. A method of controlling pests which comprises applying an effective amount of a pesticidal composition comprising:

(i) 2-methyl-4-oxo-3-(2-propynyl)cyclopent-2-enyl 3-(2,2-dichlorovinyl)-2,2-dimethylcyclopropanecarboxylate, and (ii) a propylene glycol monoalkyl ether or a dipropylene glycol monoalkyl ether to a pest or a locus where the pest inhabits.

10. The method according to claim 9, wherein the pest is a cockroach.

* * * * *